United States Patent
Ward et al.

(10) Patent No.: US 10,406,294 B2
(45) Date of Patent: Sep. 10, 2019

(54) BOOT REMOVER

(71) Applicant: Sanofi-Aventis Deutschland GmbH, Frankfurt am Main (DE)

(72) Inventors: Chris Ward, Dennbigshire (GB); Gareth Roberts, Wrexham (GB); Graham Wilson, Flintshire (GB); Troy Baker, Denbighshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 96 days.

(21) Appl. No.: 15/037,901

(22) PCT Filed: Nov. 25, 2014

(86) PCT No.: PCT/EP2014/075555
§ 371 (c)(1),
(2) Date: May 19, 2016

(87) PCT Pub. No.: WO2015/078866
PCT Pub. Date: Jun. 4, 2015

(65) Prior Publication Data
US 2016/0354550 A1    Dec. 8, 2016

(30) Foreign Application Priority Data
Nov. 28, 2013 (EP) .................. 13194891

(51) Int. Cl.
*A61M 5/32* (2006.01)
*A61M 5/00* (2006.01)
*A61M 5/31* (2006.01)

(52) U.S. Cl.
CPC .......... *A61M 5/3204* (2013.01); *A61M 5/002* (2013.01); *A61M 5/326* (2013.01);
(Continued)

(58) Field of Classification Search
CPC .. A61M 2005/3247; A61M 2005/3267; A61M 5/002; A61M 5/3202;
(Continued)

(56) References Cited

U.S. PATENT DOCUMENTS 7,771,397 B1* 8/2010 Olson ................. A61M 5/3202
604/192
2010/0069846 A1   3/2010 Stamp
(Continued)

FOREIGN PATENT DOCUMENTS

EP          0518416      12/1992
JP          H8-507239    8/1996
(Continued)

OTHER PUBLICATIONS

International Search Report and Written Opinion in International Application No. PCT/EP2014/075555, dated Jan. 29, 2015, 10 pages.
(Continued)

*Primary Examiner* — Brandy S Lee
(74) *Attorney, Agent, or Firm* — Fish & Richardson P.C.

(57) ABSTRACT

The invention relates to a boot remover (10) for removing a protective needle boot (11) from a drug delivery device (1), wherein the boot remover (10) is substantially sleeve shaped with an internal diameter and a length adapted to receive and substantially cover a needle shield (4), wherein the boot remover (10) is arranged to engage the protective needle boot (11) when attacked to the drug delivery device (1). Furthermore, the invention relates to a drug delivery device (1) comprising a boot remover (10).

18 Claims, 5 Drawing Sheets
Specification includes a Sequence Listing.

(52) U.S. Cl.
CPC ......... *A61M 5/3257* (2013.01); *A61M 5/3202* (2013.01); *A61M 2005/3125* (2013.01); *A61M 2005/3247* (2013.01); *A61M 2005/3267* (2013.01)

(58) Field of Classification Search
CPC .. A61M 5/3204; A61M 5/3257; A61M 5/326; A61M 2005/3125
See application file for complete search history.

(56) References Cited

U.S. PATENT DOCUMENTS

| | | | |
|---|---|---|---|
| 2013/0204229 A1* | 8/2013 | Olson | A61M 5/3213 604/506 |
| 2013/0310745 A1 | 11/2013 | Latham et al. | |

FOREIGN PATENT DOCUMENTS

| | | | |
|---|---|---|---|
| JP | 2013-508032 | 3/2013 | |
| JP | 2013-524916 | 6/2013 | |
| WO | WO 94/27660 | 12/1994 | |
| WO | WO 2011/047298 | 4/2011 | |
| WO | WO-2011047298 A2 * | 4/2011 | .......... A61M 5/3129 |
| WO | WO 2011/131996 | 10/2011 | |
| WO | WO2012/073032 | 7/2012 | |

OTHER PUBLICATIONS

International Preliminary Report on Patentability in International Application No. PCT/EP2014/075555, dated May 31, 2016, 7 pages.
Rote Liste, "50. Hypophysen-, Hypothalamushormone, andere regulatorische Peptide u. ihre Hemmstoffe," Chapter 50, ed. 2008, 20 pages.

* cited by examiner

SEQUENCE LISTING

<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Exendin-4(1-39), insulin analogue or derivative

<400> SEQUENCE: 1

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

BOOT REMOVER

CROSS-REFERENCE TO RELATED APPLICATIONS

This application is a U.S. national stage application under 35 USC § 371 of International Application No. PCT/EP2014/075555, filed on Nov. 25, 2014, which claims priority to European Patent Application No. 13194891.1, filed on Nov. 28, 2013, the entire contents of which are incorporated herein by reference.

TECHNICAL FIELD

The present invention relates to a boot remover for removing a protective needle boot from a drug delivery. Furthermore, the present invention relates to a drug delivery device comprising a boot remover.

BACKGROUND OF THE INVENTION

Pre-filled syringes that are filled with a selected dosage of a medicament are well known injection devices for administering the medicament to a patient. Drug delivery devices comprising a needle shield for covering a needle of a pre-filled syringe before and after use are also well known. Typically, the needle shield is either manually moved or moved by the action of a relaxing spring to surround the needle.

A different type of drug delivery device known in the state of the art solves the object of providing needle safety by arranging the pre-filled syringe movable relative to a body, whereas the pre-filled syringe is retracted into the body after the injection.

SUMMARY OF THE INVENTION

Certain aspect of the invention relate to devices for removing a protective needle boot from a drug delivery device and to related drug delivery devices.

Preferred embodiments of the invention are given in the dependent claims.

In the context of this specification, the terms distal and proximal are defined from the point of view of a person performing an injection. Consequently, a distal direction refers to a direction pointing towards the body of a patient receiving an injection and a distal end defines an end of an element that is directed towards the body of the patient. Respectively, the proximal end of an element or the proximal direction is directed away from the body of the patient receiving the injection and opposite to the distal end or distal direction.

According to the invention a boot remover is provided for removing a protective needle boot from a drug delivery device, wherein the boot remover is substantially sleeve shaped with an internal diameter and a length adapted to receive and substantially cover a needle shield, wherein the boot remover is arranged to engage the protective needle boot when attached to the drug delivery device.

The boot remover may be applied with a drug delivery device for dispensing a dose of a drug, comprising:
- a support body having a first end defining a first opening and a second end defining a second opening,
- a syringe barrel sealed by a stopper slidably disposed therein along an axial direction and adapted to have an integrated needle or to be coupled with a needle assembly comprising a needle, wherein the syringe barrel is positioned within the support body,
- a protective needle boot arrangeable over the needle on the syringe barrel,
- a needle shield adapted to be coupled to one of the ends of the support body and slidably disposed thereon for covering or exposing the needle; and
- the boot remover arrangeable over the needle shield to receive and substantially cover the needle shield, wherein the boot remover is arranged to engage the protective needle boot.

The boot remover prevents a user from holding the needle shield such that the support body cannot be moved in a distal direction with respect to the needle shield prior to removal of the boot remover and the protective needle boot. Hence, as the user must hold the support body the syringe barrel and the support body remain in place relative to the needle shield. The protective needle boot is thus removed without prematurely exposing the needle.

In an exemplary embodiment the boot remover comprises a clamping collar arranged to engage a coupling protrusion of the protective needle boot, such that the protective needle boot is axially coupled to the boot remover. The clamping collar may be arranged to allow rotation of the protective needle boot relative to the boot remover. Hence, the protective needle boot is prevented from rotating relative to the syringe and needle when being removed thus avoiding needle distortion and other damage to the needle which could otherwise cause pain to a patient when used for an injection.

The coupling protrusion of the protective needle boot may be mushroom-shaped for engaging in a bore within the clamping collar. This facilitates assembly of the boot remover on the protective needle boot and allows relative rotation between the two components.

In alternative embodiments the boot remover may be arranged to engage the protective needle boot by friction and/or by at least one barb engageable in a recess or behind a shoulder on the protective needle boot. Likewise the boot remover may be arranged as a handle integrally shaped with the protective needle boot.

In an exemplary embodiment the boot remover may comprise a direction indicator such as an arrow for indicating the direction in which the user has to move the boot remover for removing the protective needle boot.

In an exemplary embodiment the boot remover comprises at least one grip feature facilitating handling of the boot remover.

The clamping collar may form a recess with the coupling protrusion located in the centre thus communicating to the user that there is a sharp needle behind. This improves the user's telling the distal from the proximal end of the drug delivery device 1.

In an exemplary embodiment the drug delivery device may comprise an outer body coupled to the other end of the support body and slidably disposed thereon. The outer body may be grabbed by the user for applying the drug delivery device against the injection site.

A plunger rod may be coupled to the stopper, wherein a proximal portion of the plunger rod is adapted to be coupled to the outer body. This allows for displacing the drug from the cavity within the syringe barrel by applying a force to the outer body.

A detent mechanism may be arranged to constrain movement of the outer body relative to the support body. On application of the drug delivery device against the injection site the needle shield moves thus prior to the outer body relative to the support body thus preventing a so called wet injection with drug leaking out of the tip of the needle before the needle reaches an insertion depth.

In an exemplary embodiment a sleeve may be arrangeable or arranged over the support body and over the outer body, if applicable. The sleeve may be open at its distal end and abut the boot remover. The sleeve is placed over the support body and the outer body at the time of the manufacture and forms a structural exterior package. In order to use this embodiment of the drug delivery device the user holds the boot remover with one hand and the sleeve with the other and pulls the two parts apart thereby removing the sleeve in a proximal direction.

In an exemplary embodiment the sleeve may be transparent.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION OF PREFERRED EMBODIMENTS

Figure 1:
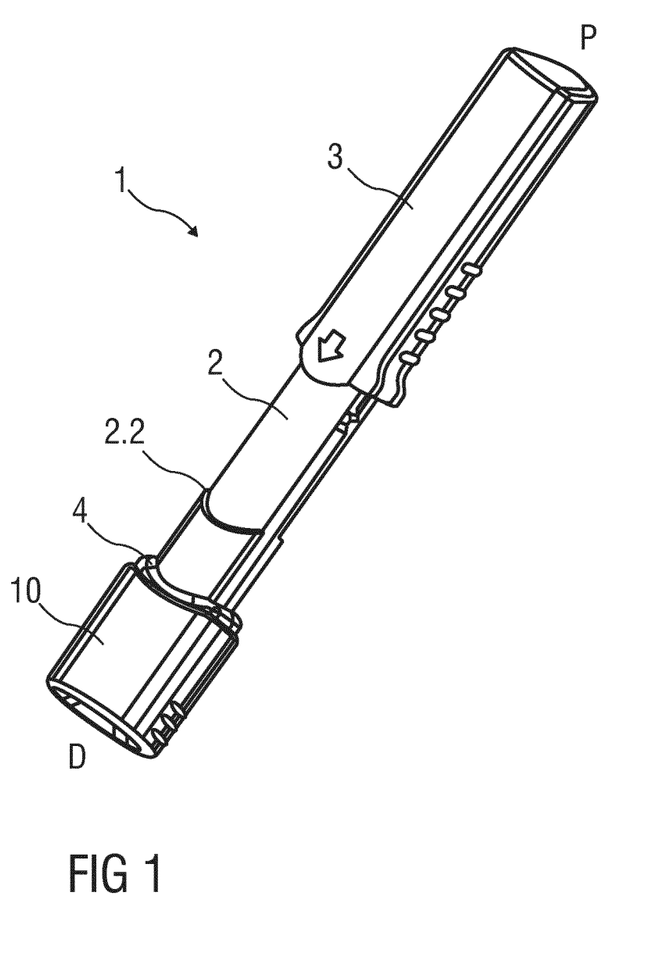
FIG. 1 is a perspective view of a drug delivery device comprising a support body, an outer body, a needle shield and a boot remover in an initial state.
Figure 2:
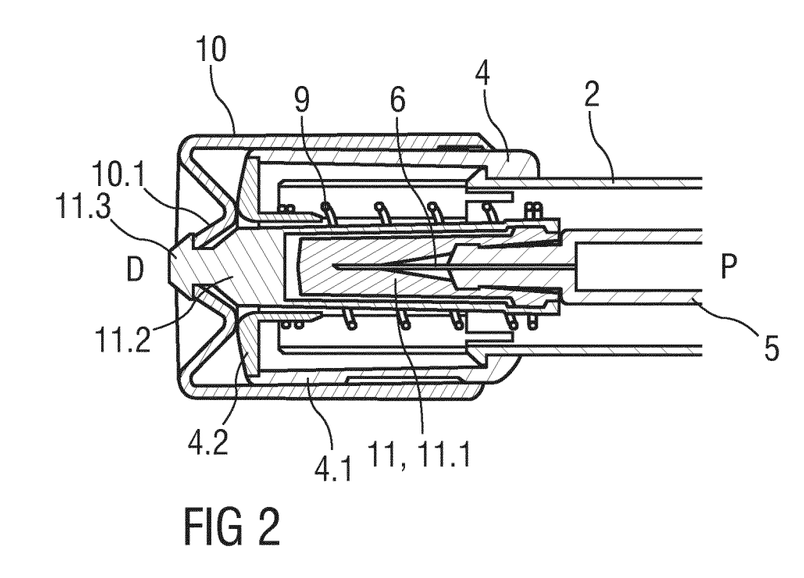
FIG. 2 is a longitudinal section of a detail of the drug delivery device.

FIG. 1 is a perspective view of a drug delivery device 1 comprising a support body 2, an outer body 3 and a needle shield 4, all of them having an essentially tubular shape. FIG. 2 is a longitudinal section of a detail of the drug delivery device 1. A proximal end of the support body 2 is telescoped in the outer body 3 and a distal end of the support body 2 is telescoped in the needle shield 4. A syringe barrel 5 is slidably arranged within the support body 2, the syringe barrel 5 defining an inner cavity for a dose of a drug. A hollow injection needle 6 is arranged on a distal end of the syringe barrel 5. A stopper (not illustrated) is slidably arranged within the syringe barrel 5 for sealing its proximal end and for displacing the drug from the syringe barrel 5 through the injection needle 6. A plunger rod (not illustrated) is arranged within the outer body 2 for engaging the stopper. The plunger rod may be screwed or snapped into the stopper. A needle shield spring 9 is arranged for biasing the needle shield 4 in the distal direction D against the support body 2.

The outer body 3 is movable in a distal direction D and in a proximal direction P with respect to the support body 2.

The syringe barrel 5 is inserted into the support body 2 and fixed towards the distal direction D in its axial position with respect to the support body 2.

The support body 2 comprises an indicator ring 2.2 in the shape of radially outwards protruding and essentially circumferential rib. The indicator ring 2.2 may cover part of or the whole circumference of the support body 2. The indicator ring 2.2 is arranged to interact with the needle shield 4 so as to limit distal movement of the support body 2 with respect to the needle shield 4. Furthermore, the support body 2 comprises a locking mechanism and linear guide rails (not illustrated) that run in an axial direction for providing a staged movement between the support body 2, the outer body 3 and the needle shield 4.

The needle shield 4 comprises a tubular body section 4.1 and a cap part 4.2 with a central opening 4.3. The cap part 4.2 is engaged to the body section 4.1 by a snap fit (not illustrated) thus preventing relative axial movement. A protective needle boot 11 may be positioned over the needle 6 on the syringe barrel 5 in and/or through the central opening 4.3 of the cap part 4.2 before and after an injection. The cap part 4.2 is rotationally locked to the body section 4.1. This may be achieved by the cap part 4.2 having a non-circular, e.g. elliptical cross section engaging in a corresponding opening in the body section 4.1.

Figure 3:
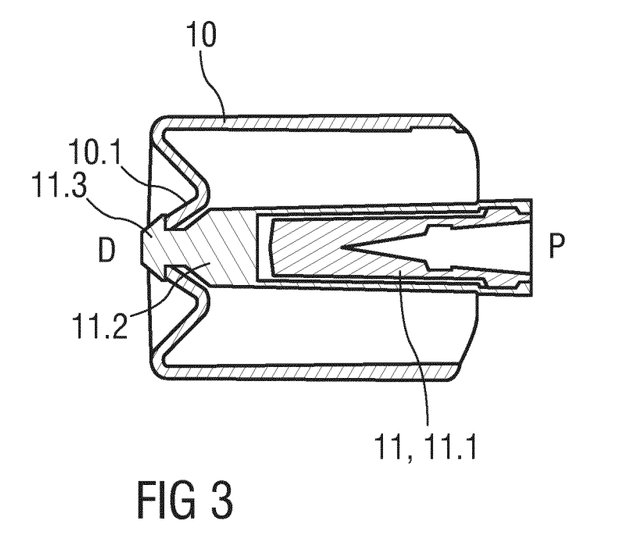
FIG. 3 is a longitudinal section of the boot remover with a protective needle boot.

The protective needle boot 11 comprises an inner boot 11.1 which may comprise or consist of a resilient material and an outer boot 11.2 which is more rigid and arranged over the inner boot 11.1, wherein the inner boot 11.1 and outer boot 11.2 are positively and or non-positively coupled to each other. At a distal end of the outer boot 11.2 a coupling protrusion 11.3 is arranged. In an exemplary embodiment the coupling protrusion 11.3 is mushroom shaped. The mushroom-shaped coupling protrusion 11.3 and/or the clamping collar 10.1 may comprise one or more longitudinal slots for allowing them to deflect during assembly.

A boot remover 10 is arranged for removing the protective needle boot 11 prior to an injection. The boot remover 10 is substantially sleeve shaped with an internal diameter and a length adapted to receive the needle shield 4 and substantially cover the needle shield 4 such that the needle shield 4 cannot be grabbed by a user when arranged within the boot remover 10. A clamping collar 10.1 in the distal end of the boot remover 10 is arranged to engage the coupling protrusion 11.3 of the protective needle boot 11, such that the protective needle boot 11 is axially coupled to the boot remover 10 but free to rotate relative to the boot remover 10. FIG. 3 is a longitudinal section of the boot remover 10 with the protective needle boot 11.

In alternative embodiments the boot remover 10 may be arranged to engage the protective needle boot 11 by friction and/or by means of barbs. A direction indicator may be provided on the boot remover 10 for indicating the direction in which the user has to move the boot remover 10 for removing the protective needle boot 11. Likewise the boot remover 10 may be arranged as a handle integrally shaped with the protective needle boot 11.

FIGS. 1 and 2 show the drug delivery device 1 prior to an injection. The outer body 3 is fully extended in the proximal direction P from the support body 2. The needle shield 4 is fully extended from the support body 2 in the distal direction D. The injection needle 6 is in a retracted position within the needle shield 4. The needle shield spring 9 is relaxed.

A user may grab the outer body 3 or the support body 2 and pull the boot remover 10 in the distal direction D for removing the protective needle boot 11.

Consequently, the boot remover 10 will be pulled off the needle shield 4 and the protective needle boot 11 will be pulled out of the central opening 4.3 of the needle shield 4.

Figure 4:
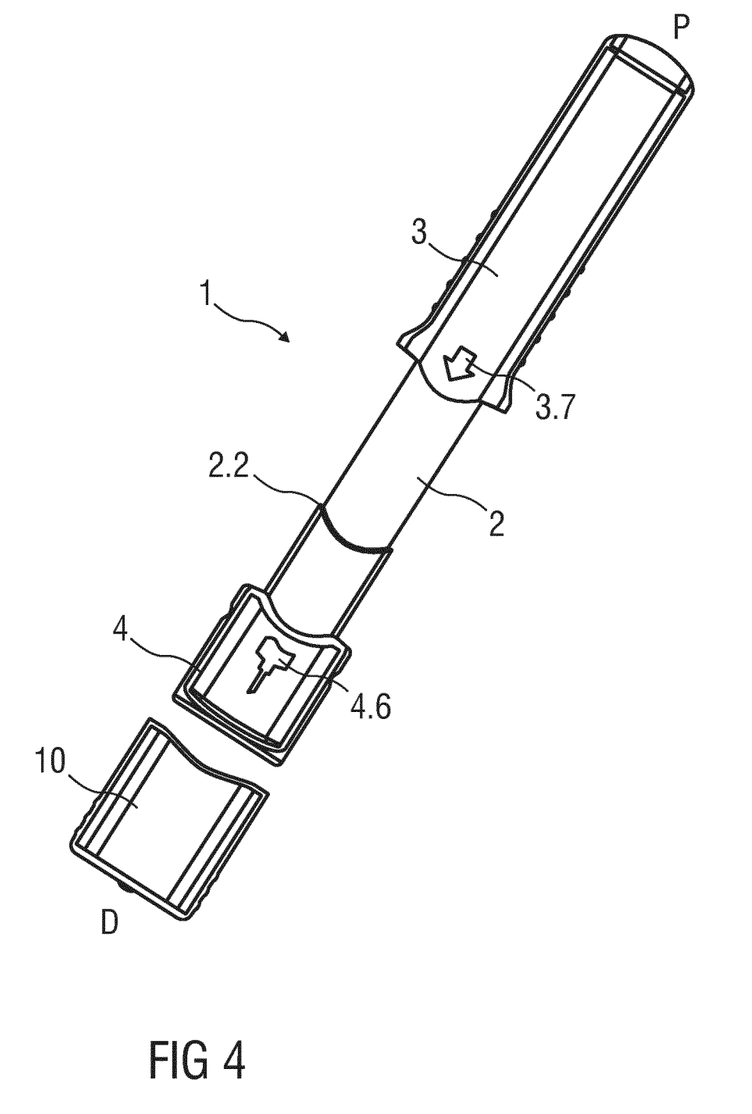
FIG. 4 is a side view of the drug delivery device after removal of the boot remover.
Figure 5:
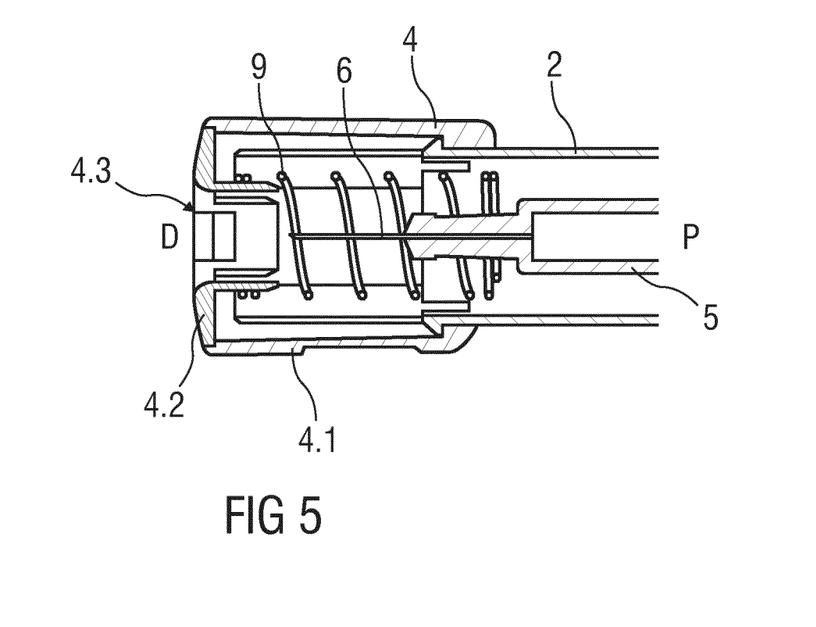
FIG. 5 is a longitudinal section of a detail of the drug delivery device after removal of the boot remover and the protective needle boot.

If the user could hold the needle shield 4 while pulling the boot remover 10 friction between the protective needle boot 11 and the syringe barrel 5 would tend to pull the syringe barrel 5 and hence the support body 2 in the distal direction D relative to the needle shield 4 which would result in premature exposure of the needle 6. However, due to the boot remover 10 preventing the user from holding the needle shield 4 the support body 2 cannot be moved in the distal direction D with respect to the needle shield 4. Hence, as the user must hold either the support body 2 or the outer body 3 the syringe barrel 5 and the support body 2 remain in place. The protective needle boot 11 is thus removed without exposing the needle 6 as illustrated in FIGS. 4 and 5.

The user may now push the distal end of the needle shield 4 against an injection site, e.g. a patient's skin. The force from the user's hand is resolved through the outer body 3, the support body 2, into the needle shield 4. As the user applies a sufficiently high force the needle shield 4 is moved in the proximal direction P with respect to the support body 2 and all other parts of the drug delivery device 1 thereby also compressing the needle shield spring 9.

On application of the drug delivery device 1 against the patient's skin the needle shield 4 moves prior to the outer body 3 relative to the support body 2 due to a locking mechanism or detent (not illustrated) between the support body 2 and the outer body 3. This movement is opposed by the friction force of the injection needle 6 when penetrating the skin. In order to avoid a so called wet injection with drug leaking out of the tip of the needle during needle insertion before reaching the insertion depth the friction force of the needle 6 must be less than the counteracting force of the stopper 7 due to friction between the stopper 7 and the inner wall of the syringe 5 and due to the hydrostatic resistance of the drug to be displaced through the hollow needle 6, which depends on the inner diameter of the needle 6 and the viscosity of the drug. The needle insertion depth is defined by the needle shield 4 abutting the indicator ring 2.2. The mating surfaces of the indicator ring 2.2 and the needle shield 4 visually and haptically indicate to the user that they are intended to be pushed completely together in order to correctly apply the drug delivery device 1.

Once insertion depth has been reached, further application of force onto the outer body 3 overcomes the detent so that the outer body 3 decouples from the support body 2 and moves relative to the support body 2 in the distal direction D thus also moving the stopper 7 within the syringe barrel 5 so that the drug is displaced from the cavity through the injection needle 6. Near the end of the injection the stopper 7 bottoms out in the syringe barrel 5. At the same time the outer body 3 abuts the indicator ring 2.2. The mating surfaces of the indicator ring 2.2 and the outer body 3 visually and haptically indicate to the user that they are intended to be pushed completely together in order to correctly apply the drug delivery device 1.

If the user removes the drug delivery device 1 from the injection site the needle shield 4 is no longer pushed against the skin and is hence extended in the distal direction D relative to the other components of the drug delivery device 1 by the needle shield spring 9 such that the injection needle 6 arrives fully inside the needle shield 4. A locking mechanism may be provided between the needle shield 4 and the support body 2 for preventing the needle shield 4 from being retracted once more.

The end of the outer body 3 coupled to the support body 2 may comprise a radially outwards directed flange 3.6 thus improving ergonomics when applying the drug delivery device 1.

In an exemplary embodiment a direction indicator 3.7 designed as a profiled cavity or concavity in the surface of the outer body 3 is arranged in the range of the flange 3.6.

The needle shield 4 may likewise comprise a direction indicator 4.6.

A label retaining recess may be arranged in the outer body 3 for receiving a label which may be customized to the drug to be delivered and/or to the provider of the drug.

Figure 6:
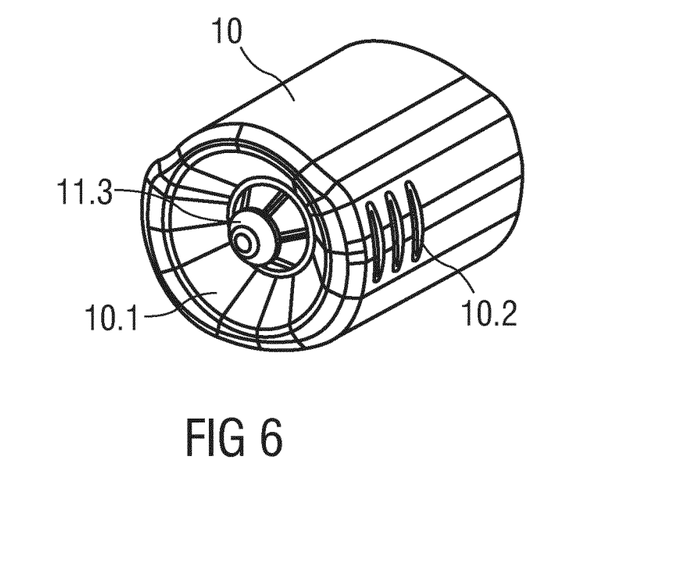
FIG. 6 is a perspective view of an exemplary embodiment of the boot remover with grip features.

FIG. 6 is a perspective view of an exemplary embodiment of the boot remover 10. The boot remover 10 comprises grip features 10.2 facilitating handling of the boot remover 10. The clamping collar 10.1 forms a recess with the coupling protrusion 11.3 in the centre thus communicating to the user that there is a sharp needle 6 behind. This improves the user's telling the distal from the proximal end of the drug delivery device 1.

Figure 7:
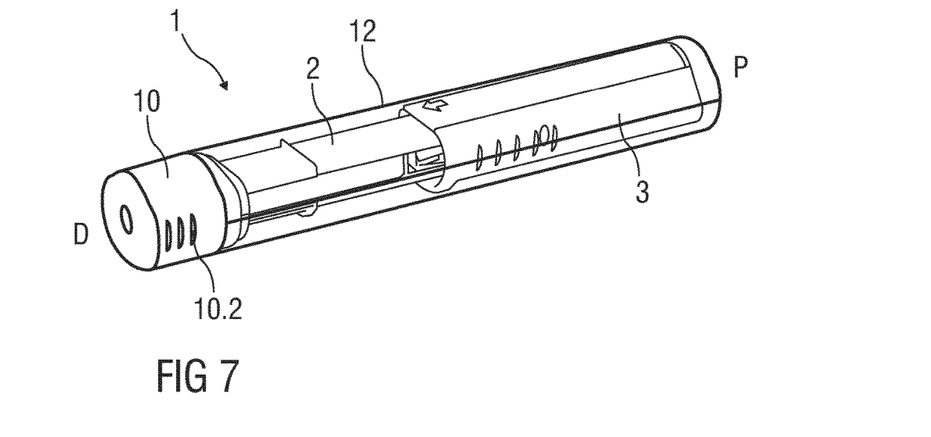
FIG. 7 is a perspective view of an exemplary embodiment of the drug delivery device with an additional transparent sleeve arranged over the support body.
Figure 8:
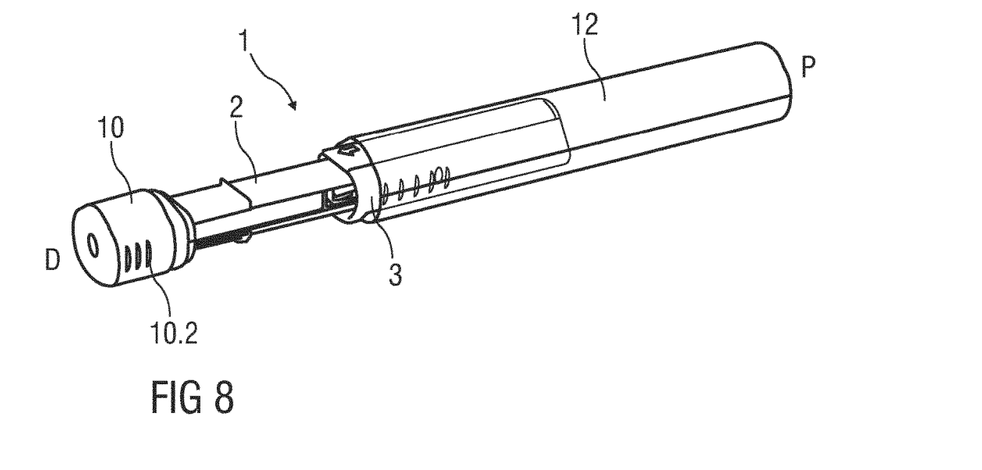
FIG. 8 is a perspective view of the drug delivery device from FIG. 7 during removal of the transparent sleeve.

FIG. 7 is a perspective view of an exemplary embodiment of the drug delivery device 1 with an additional transparent sleeve 12 arranged over the support body 2 and the outer body 3. The sleeve 12 is open at its distal end and abuts the boot remover 10. The sleeve 12 is placed over the support body 2 and the outer body 3 at the time of the manufacture and forms a structural exterior package. In order to use this embodiment of the drug delivery device 1 the user holds the boot remover 10 with one hand and the sleeve 12 with the other and pulls the two parts apart thereby removing the transparent sleeve 12 in the proximal direction P. FIG. 8 is a perspective view of this embodiment of the drug delivery device 1 during removal of the transparent sleeve 12.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2 (SEQ ID NO:1).

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(02)25, Asp28] Exendin-4(1-39),
des Pro36 [Met(O)14 Trp(02)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(02)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

LIST OF REFERENCES 1 drug delivery device
2 support body
2.2 indicator ring
2.4 internal rib
3 outer body
3.6 flange
3.7 direction indicator
4 needle shield
4.1 body section
4.2 cap part
4.3 central opening
4.6 direction indicator
5 syringe barrel
5.1 barrel collar
6 needle
9 needle shield spring
10 boot remover
10.1 clamping collar
10.2 grip feature
11 protective needle boot
11.1 inner boot
11.2 outer boot
11.3 coupling protrusion
12 sleeve
D distal direction
P proximal direction

The invention claimed is:

1. A drug delivery device for dispensing a dose of a drug, comprising:
   a support body having a first end defining a first opening and a second end defining a second opening,
   a syringe barrel sealed by a stopper slidably disposed therein along an axial direction and adapted to have an integrated needle or to be coupled with a needle assembly comprising a needle, wherein the syringe barrel is positioned within the support body,
   a protective needle boot arrangeable over the needle on the syringe barrel,
   a needle shield adapted to be coupled to one of the first end and the second end of the support body and slidably disposed relative to the support body for covering or exposing the needle,
   an outer body coupled to the other of the first end and the second end of the support body and slidably disposed relative to the support body; and
   a boot remover for removing the protective needle boot from the syringe barrel, the boot remover comprising a clamping collar arranged to engage a coupling protrusion of the protective needle boot, such that the protective needle boot is axially coupled to the boot remover, wherein the boot remover is substantially sleeve shaped with an internal diameter and a length adapted to receive and substantially cover the needle shield, wherein the boot remover is arranged to engage the protective needle boot when attached to the drug delivery device.

2. The drug delivery device according to claim 1, wherein the clamping collar is arranged to allow rotation of the protective needle boot relative to the boot remover.

3. The drug delivery device according to claim 2, wherein the coupling protrusion of the protective needle boot is mushroom-shaped for engaging in a bore within the clamping collar.

4. The drug delivery device according to claim 1, wherein the boot remover is arranged to engage the protective needle boot by friction.

5. The drug delivery device according to claim 1, wherein the boot remover is arranged as a handle integrally shaped with the protective needle boot.

6. The drug delivery device according to claim 1, comprising a direction indicator for indicating a direction for removing the protective needle boot.

7. The drug delivery device according to claim 1, comprising at least one grip feature.

8. The drug delivery device according to claim 1, wherein the clamping collar forms a recess with the coupling protrusion located in a center of the clamping collar.

9. The drug delivery device according to claim 1, wherein the coupling protrusion is arranged at a distal end of the protective needle boot.

10. The drug delivery device according to claim 1, wherein a plunger rod is coupled to the stopper, and wherein a proximal portion of the plunger rod is adapted to be coupled to the outer body.

11. The drug delivery device according to claim 1, wherein a detent mechanism is arranged to constrain movement of the outer body relative to the support body.

12. The drug delivery device according to claim 1, wherein a sleeve is arrangeable over the support body.

13. The drug delivery device according to claim 12, wherein the sleeve is transparent.

14. The drug delivery device according to claim 1, wherein the syringe barrel contains a pharmaceutically active compound.

15. The drug delivery device according to claim 1, wherein the boot remover is arranged to engage the protective needle boot by friction and by at least one barb engageable in a recess or behind a shoulder on the protective needle boot.

16. The drug delivery device according to claim 1, wherein the boot remover is arranged to engage the protective needle boot by at least one barb engageable in a recess or behind a shoulder on the protective needle boot.

17. The drug delivery device according to claim 1, wherein the needle shield is configured to move from an extended position, in which the needle shield covers the needle, to an retracted position, in which the needle shield exposes the needle, and wherein the needle shield is directly coupled to the support body in the retracted and extended positions.

18. The drug delivery device according to claim 1, wherein the needle shield is slidably attached to the support body.

* * * * *

UNITED STATES PATENT AND TRADEMARK OFFICE
CERTIFICATE OF CORRECTION

PATENT NO. : 10,406,294 B2
APPLICATION NO. : 15/037901
DATED : September 10, 2019
INVENTOR(S) : Chris Ward et al.

Page 1 of 1

It is certified that error appears in the above-identified patent and that said Letters Patent is hereby corrected as shown below:

On the Title Page

Column 1, Item (72), Line 1, under "Inventors", delete "Dennbigshire" and insert -- Denbighshire --.

Column 2, Item (57), Line 7, under "ABSTRACT", delete "attacked" and insert -- attached --.

Signed and Sealed this
Twenty-fourth Day of December, 2019

Andrei Iancu
*Director of the United States Patent and Trademark Office*